United States Patent
Bill et al.

(10) Patent No.: US 11,541,185 B2
(45) Date of Patent: Jan. 3, 2023

(54) INJECTION DEVICE AND CORRESPONDING INJECTION-MEASURING METHOD

(71) Applicant: Robert Bosch GmbH, Stuttgart (DE)

(72) Inventors: David Bill, Rheinhausen (DE); Philipp Troebner, Frankfurt (DE)

(73) Assignee: Robert Bosch GmbH, Stuttgart (DE)

( * ) Notice: Subject to any disclaimer, the term of this patent is extended or adjusted under 35 U.S.C. 154(b) by 459 days.

(21) Appl. No.: 16/640,251

(22) PCT Filed: Aug. 9, 2018

(86) PCT No.: PCT/EP2018/071578
§ 371 (c)(1),
(2) Date: Feb. 19, 2020

(87) PCT Pub. No.: WO2019/042732
PCT Pub. Date: Mar. 7, 2019

(65) Prior Publication Data
US 2020/0246548 A1 Aug. 6, 2020

(30) Foreign Application Priority Data
Aug. 29, 2017 (DE) ...................... 10 2017 215 035.1

(51) Int. Cl.
*A61M 5/315* (2006.01)
(52) U.S. Cl.
CPC ...... *A61M 5/3155* (2013.01); *A61M 5/31528* (2013.01); *A61M 5/31568* (2013.01);
(Continued)
(58) Field of Classification Search
CPC ............ A61M 5/3155; A61M 5/31528; A61M 5/31568; A61M 2205/3306;
(Continued)

(56) References Cited

U.S. PATENT DOCUMENTS

2003/0193015 A1\* 10/2003 Chong .................. G01D 5/347
250/231.13
2015/0202377 A1 7/2015 Haupt
(Continued)

FOREIGN PATENT DOCUMENTS

| CN | 101162156 A | 4/2008 |
| CN | 101608931 A | 12/2009 |

(Continued)

OTHER PUBLICATIONS

International Search Report for PCT/EP2018/071578, dated Oct. 24, 2018.

*Primary Examiner* — Tasnim Mehjabin Ahmed
(74) *Attorney, Agent, or Firm* — Norton Rose Fulbright US LLP; Gerard Messina (57) ABSTRACT

An injection-device and an injection-measuring method are described. The injection-device includes a pen-type sleeve for accommodating a cartridge holder, a mechanical injection system provided in the pen-type sleeve, which has a dosing sleeve by which a dosage quantity to be injected is predefinable and which is configured to execute a rotatory motion during the injection process; a selector device, connected to the dosing sleeve, for adjusting the dosage quantity to be injected; an injection button, connected to the selector device, for applying an injection force; and an optical sensor device for detecting the rotatory motion of the dosage sleeve during injection of the dosage quantity, which has a signal-processing device for ascertaining and storing the injected dosage quantity based on the detected rotatory motion of the dosage sleeve. The injection button has a switch device by which the optical sensor device is activatable when applying the injection force.

12 Claims, 6 Drawing Sheets

(52) U.S. Cl.
CPC ............... *A61M 2205/3306* (2013.01); *A61M 2205/3584* (2013.01); *A61M 2205/50* (2013.01); *A61M 2205/52* (2013.01)

(58) Field of Classification Search
CPC ...... A61M 2205/3584; A61M 2205/50; A61M 2205/52
See application file for complete search history.

(56) References Cited

U.S. PATENT DOCUMENTS

| | | |
|---|---|---|
| 2016/0015902 A1 | 1/2016 | Draper |
| 2016/0213856 A1 | 7/2016 | Despa et al. |
| 2018/0250473 A1* | 9/2018 | Ganzitti ............ A61M 5/31585 |
| 2020/0171246 A1* | 6/2020 | Byerly .............. A61M 5/31568 |

FOREIGN PATENT DOCUMENTS

| | | |
|---|---|---|
| CN | 101865704 A | 10/2010 |
| CN | 104936640 A | 9/2015 |
| DE | 102004063650 A1 | 7/2006 |
| EP | 2945674 A1 | 11/2015 |
| TW | 201534364 A | 9/2015 |
| WO | 2015075134 A1 | 5/2015 |
| WO | 2015136513 A1 | 9/2015 |
| WO | 2016131713 A1 | 8/2016 |
| WO | 2017009724 A1 | 1/2017 |
| WO | 2017066067 A1 | 4/2017 |

* cited by examiner

INJECTION DEVICE AND CORRESPONDING INJECTION-MEASURING METHOD

FIELD OF THE INVENTION

The present invention relates to an injection device and to a corresponding injection-measuring method.

BACKGROUND INFORMATION

Although various types of injection devices can be used, the present invention and the problems on which it is based are described on the basis of pen-type injection devices for delivering insulin.

Pen-type injection devices for the subcutaneous injection of liquid drugs and active ingredients such as insulin have been commercially available for many years. Such devices exist in two basic variants. For one, there is a prefilled version, which is disposed of once it is completely empty, and for another, there is a version that allows the completely empty active ingredient cartridge to be exchanged and the mechanical part to be reused.

Figure 9:
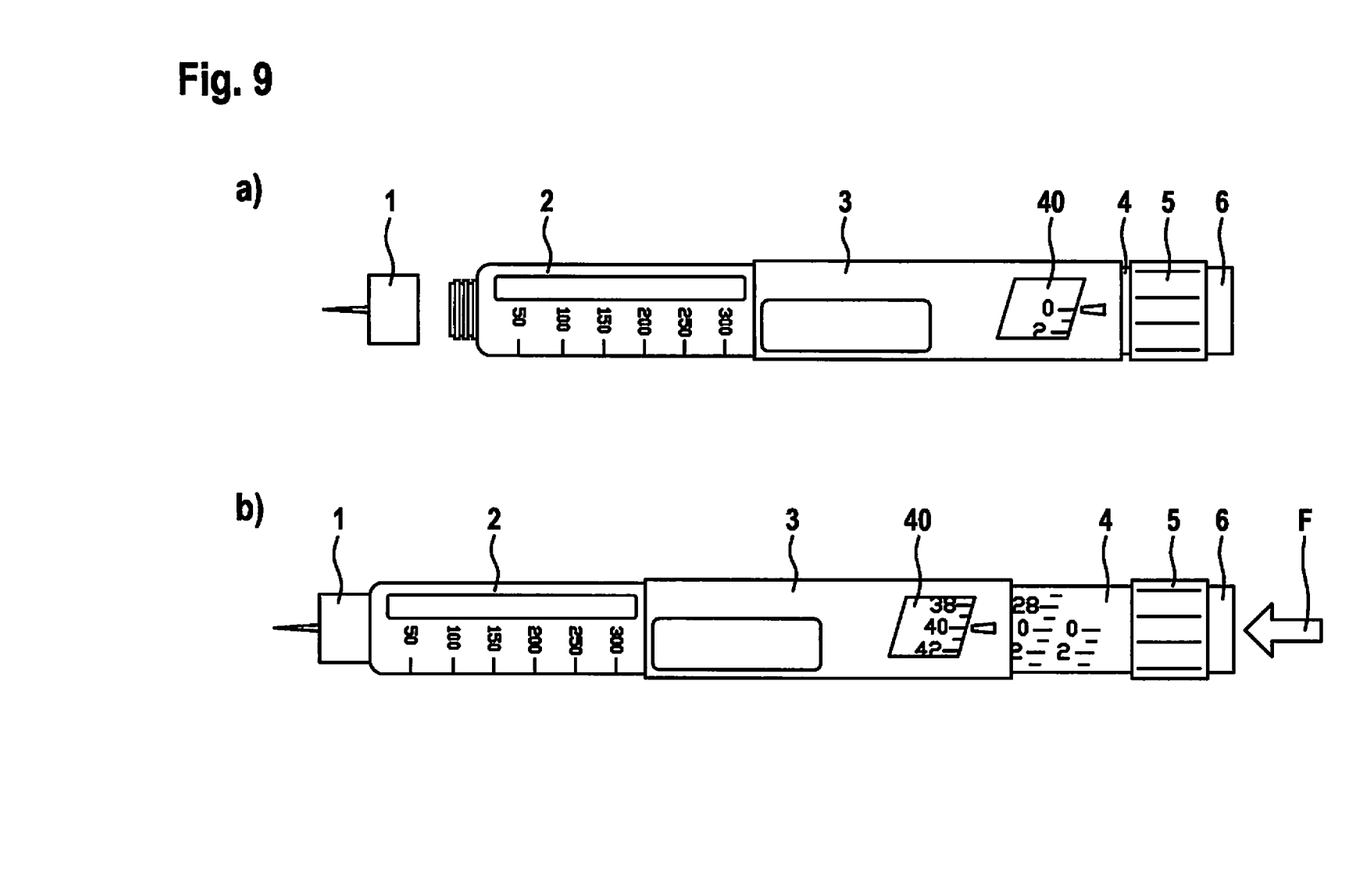
FIG. 9a) shows a schematic view of an exemplary injection device, with a preselected dosage quantity of 0 mL.
FIG. 9b) shows a schematic view of an exemplary injection device, with a preselected dosage quantity of 40 ml.

FIGS. 9a), b) are schematic views of an exemplary injection device, i.e. FIG. 9a) with a preselected dosage amount of 0 ml, and FIG. 9b) with a preselected dosage amount of 40 ml.

Reference numeral 1 in FIG. 9a), b) denotes an injection needle, which is able to be screwed onto a drug cartridge. A pen-type tube 3 has an integrated mechanical system for dosing and injecting purposes. A dosing sleeve 4, which is part of the mechanical system, is connected to a selector mechanism 5 for selecting the desired dosage amount, and after the dosage amount has been selected, it is administered to a patient through pressure on injection button 6. The mechanical system integrated into the interior of pen-type tube 3 is used for a manual adjustment of the injection quantity from the drug cartridge. During the injection process, the preselected injection quantity is mechanically transmitted onto a plunger, which expels the drug from a drug cartridge situated in cartridge holder 2.

The injection quantity is selected in particular by rotating selector mechanism 5, whereupon a display 40 shows the selected dosage amount. Together with selector mechanism 5, the dosing sleeve 4 also gets unscrewed from pen-type sleeve 3 in the process. When the injection quantity is selected, injection button 6 also moves away from pen-type tube 3. The selected dosage is able to be corrected at all times by turning selector mechanism 5 in the opposite direction. Through the application of a force F in the axial direction in relation to injection button 6, as indicated by the black arrow in FIG. 9b), the drug is able to be injected via needle 1. Depending on the development, there are certain mechanical components that execute rotatory and translatory motions during the injection using such an injection device, while others execute translatory motions exclusively.

For example, selector mechanism 5 may form a fixed unit with injection button 6. By applying axially directed force F on injection button 6, this unit made up of selector mechanism 5 and injection button 6 executes a translatory motion in the direction of pen-type tube 3, whereas dosing sleeve 4 is moved both in a translatory and a rotatory fashion.

On the other hand, it is also possible for selector mechanism 5 to be fixedly connected to dosing sleeve 4 and then to carry out the rotatory and translatory motions together with it, whereas injection button 6 executes a translation exclusively.

Since from a medical standpoint better therapy approaches require a complete data profile of a patient, there are various approaches for reading out this purely mechanical solution with the aid of an optical sensor system and for then processing it further.

The sensor-based detection of a translatory and rotatory change in position with the aid of optical systems is generally known in the related art. For example, optical incremental encoders are used to detect angles of rotation or angular velocities or rotational speeds. Systems of this type are used in mechanical drive systems among other applications.

The document US 2016/0015902 A1 discusses a setup having two optical sensors for a dosage determination and for differentiating between a dosage selection and dose dispensing using corresponding drug-dispensing devices. The optical sensor used for determining the dosage is directed toward a rotatable component of the injection device, which moves either in a rotatory and translatory fashion or only in a translatory fashion relative to this sensor both when selecting the dosage and dispensing the dosage. The sensor for determining the dosage is connected to the outer housing or to the pen-type sleeve, and it is situated either in a recess of the outer housing or on the inner surface thereof, or is even a part of an additional device which is able to be mounted on the pen-type sleeve in a detachable manner.

The document WO 2015/136513 A1 discusses an optical sensor for an injection device which detects the dosage set during the dosage selection. Through an additional acceleration sensor, it is determined whether this quantity is actually also dispensed or whether an adaptation is made to the selected dosage. This system is attached to a corresponding injection device as a retrofitting solution.

The document WO 2017/009724 A1 discusses a system that is able to be mounted on an injection device and optically senses the position of the plunger that pushes the drug out of the cartridge. This makes it possible to determine the quantity of the dispensed drug.

The document US 2015/0202377 A1 discusses a retrofitting device for an injection device, which acquires an image of the dosing window and detects the adjusted quantity using optical character recognition.

The retrofittable devices are believed to constitute a cumbersome and awkward supplement to injector devices.

SUMMARY OF THE INVENTION

The present invention provides an injection device as described herein as well as a corresponding injection-measuring method as described herein.

Further developments are the subject matter of the respective further descriptions herein.

The present invention is based is the compact integration of an optical sensor system into an injection device, the optical sensor system detecting a rotation of a component which is rotating relative to the sensor system while the drug is dispensed. A signal processing unit is able to ascertain the dispensed dose on that basis and, if desired, to transmit it in a wireless or a wired manner to a user terminal. The required electronics may be fully integrated into the selector mechanism and/or the injection button. The injection button, for instance, may be configured to be removable in order to provide access to the electronics for the exchange of a battery, for example, and/or for the reuse of the sensor device situated in the injection button in other injection devices.

The solution according to the present invention is characterized by a very low susceptibility to failure with regard to environmental effects as well as by an uncomplicated signal evaluation. Because the electronics are integrated into the injection button and/or the selector mechanism, the space requirement of the optical sensor system is reduced. The user friendliness is improved because there is no need to use plug-in modules or mounted modules. As a whole, the solution according to the present invention is therefore more cost-effective than known solutions.

The information made available according to the present invention is able to be used for determining the dispensed dose, the application instant, etc. As a result, it is possible to monitor whether the patient is progressing within a predefined treatment plan or to optimally adapt the treatment plan to the patient.

According to one further development, the optical sensor device has a light-transmitting device, a light-receiving device, and a light-encoding device, which are positioned in such a way that the light emitted by the light-transmitting device impinges upon the light-encoding device before it impinges upon the light-receiving device. This makes it possible to integrate the optical sensor device in a space-saving manner.

According to an additional further development, the light-encoding device is provided on or in an axial outer periphery of the dosing sleeve, and the light-transmitting device and the light-receiving device are provided in an oppositely situated region on or in the selector device, separated by an axial interspace between the dosing sleeve and the selector device, and the selector device is configured in such a way that the dosing sleeve executes the rotatory motion relative to the selector device during the injection process. This allows for a simple integration into existing components.

According to another further development, the light-encoding device is provided on or in a radial outer periphery of the dosing sleeve, and the light-transmitting device and the light-receiving device are provided in a oppositely situated region on or in the selector device, separated by a radial interspace between the dosing sleeve and the selector device, and the selector device is configured in such a way that the dosing sleeve executes the rotatory motion relative to the selector device during the injection process. In this way, the light-encoding device is able to be integrated on the topside of the dosing sleeve.

According to another further development, the light-transmitting device, the light-receiving device, and the signal-processing device are integrated into the selector device. This allows for a compact configuration.

According to another further development, the injection button is able to be removed from the selector device. In this way, the energy supply, e.g., a battery, is able to be exchanged and the sensor device may be used in other injection devices.

According to another further development, the light-encoding device is provided on or in a radial inner periphery of the selector device, and the light-transmitting device and the light-receiving device are provided in an oppositely situated region on or in the injection button, separated by a radial interspace between the selector device and the injection button, and the injection button is configured in such a way that the dosing sleeve executes the rotary motion relative to the injection button together with the selector device during the injection process. This allows for a realization in systems in which the selector device rotates during the injection process.

According to another further development, the light-transmitting device, the light-receiving device and the signal-processing device are integrated into the injection button. This allows for a miniaturized configuration.

According to another further development, the optical sensor device has an internal memory. This makes it possible to store the measured data for control purposes.

According to another further development, the optical sensor device has a wireless or wired transmission device for transmitting the ascertained injected dosage quantity to an external memory device. This allows for processing on external devices.

According to another further development, the light-encoding device, which has an annular development, includes reflective regions and non-reflective regions. In this way measured data that are not susceptible to interference are able to be generated.

Additional features and advantages of the present invention are described in the following text on the basis of specific embodiments with reference to the figures.

Matching reference numerals in the figures denote identical or functionally equivalent elements.

For reasons of a simplified representation, the injection device in the described specific embodiments already described by FIGS. 9a), 9b) is shown only partially. Reference is made to FIGS. 9a), 9b) for the components that are not illustrated.

DETAILED DESCRIPTION

Figure 1:
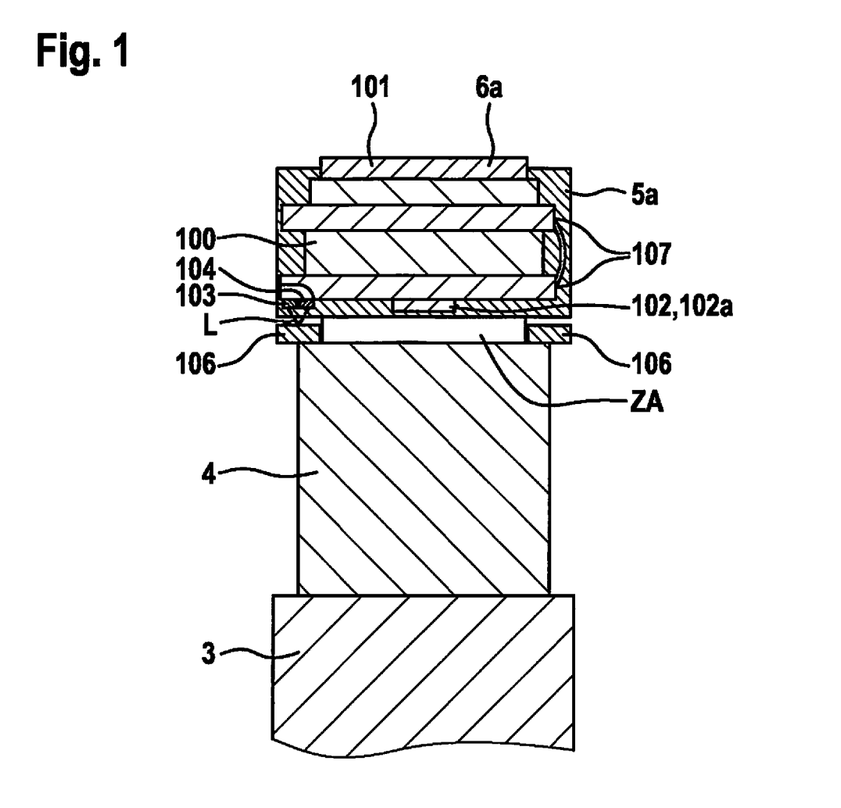
FIG. 1 shows a schematic, partial cross-sectional representation to describe an injection device according to a first specific embodiment of the present invention.

FIG. 1 is a schematic, partial cross-sectional representation to describe an injection device according to a first specific embodiment of the present invention.

As already mentioned, pen-type tube 3 is used for retaining a cartridge holder 2, which in turn may include a drug cartridge. A mechanical injection system is provided in pen-type tube 3, which includes a dosing sleeve 4 with the aid of which a dosage quantity to be injected is able to be manually predefined through a rotary motion. Dosing sleeve 4 executes a rotatory motion during the injection process, i.e. a rotatory motion relative to pen-type tube 3 and relative to the group made up of selector device 5a and injection button 6a connected thereto in the first specific embodiment in order to apply the injection force. Selector device 5a connected to dosing sleeve 4 is used for adjusting the dosage quantity to be injected, similar also to the example according to FIGS. 9a), b).

Provided in addition to the known injection device is an optical sensor device 100, 101, 102, 103, 104, 105 for detecting the rotatory motion of dosing sleeve 4 during the injection of the dosage quantity. Optical sensor device 100, 101, 102, 103, 104, 105 has an energy supply 100 such as a battery; a switch device 101 by which optical sensor device 100, 101, 102, 103, 104, 105 is activatable when the injection force is applied (e.g., mechanically, inductively, capacitively or resistively); a signal-processing device 102; a light-transmitting device 103; a light-receiving device 104; an internal memory 105 (see FIG. 3); and a light-encoding device 106.

Switch device 101 is integrated into injection button 6a or coupled to it, whereas the energy-supply device, signal-processing device 102, light-transmitting device 103 and light-receiving device 104 are integrated into selector device 5a. A circuit board device 107, which is likewise integrated into selector device 5a, is used for the corresponding retaining and electrical interconnection of the components of optical sensor device 100, 101, 102, 103, 104, 105.

Light-encoding device 106 is provided on an axial outer periphery of dosing sleeve 4, and light-transmitting device 103 and light-receiving device 104 are provided in an oppositely situated region in selector device 5a, separated by an axial interspace ZA between dosing sleeve 4 and selector device 5a.

Selector device 5a is configured in such a way that dosing sleeve 4 executes the rotatory motion in relation to selector device 5a and injection button 6a connected thereto during the injection process.

Light-transmitting device 103 emits light L of a certain wavelength or a certain wavelength range. One possible implementation of light-transmitting device 103 is an infrared LED. Light-receiving device 104 is a photodiode, a photo transistor or a digital light sensor, for example. The wavelength or the wavelength range of light-receiving device 104 is adapted to the wavelength or the wavelength range of the light-transmitting device. For instance, it is possible to select a wavelength that does not occur in the natural spectrum of the light or of artificial illumination sources or that occurs only partially, so that interference may be minimized.

The signal-processing device is used for ascertaining and storing the injected dosage quantity based on the detected rotatory motion of dosing sleeve 4. The storing takes place in internal memory 105 in the first specific embodiment. In addition, the signal-processing device includes a wireless or wired transmission device 102a for transmitting the ascertained injected dosage quantity to an external memory unit, if desired.

Moreover, even further parameters such as the injection instant, are able to be detected and stored or transmitted. Signal-processing device 102, for example, may be configured as a conventional microprocessor. Wireless or wired transmitting device 102a, for instance, may carry out a transmission of the data via Bluetooth. Injection button 6a forms a unit with selector device 5a in the first specific embodiment but may be removable in order to exchange an energy-supply device 101 in the form of a battery and to be able to use the sensor system in other injection devices. The activation of optical sensor device 100, 101, 102, 103, 104, 105 via switch device 101 makes it possible to save energy and to thereby extend the service life of energy-supply device 100.

Circuit board device 107 in selector device 5a may be configured as a firm substrate, e.g., PCB (printed circuit board) or as a plastic able to be fitted with components or as a fully or partially flexible substrate such as Flex-PCB (flexible PCB) or foil. In particular, it is not necessary to distinguish between dosage selection and dosage dispensing because no axial force is exerted on injector button 6a during the dosage selection and optical sensor device 100, 101, 102, 103, 104, 105 is thus not active because of the open position of switch device 101.

Figure 2:
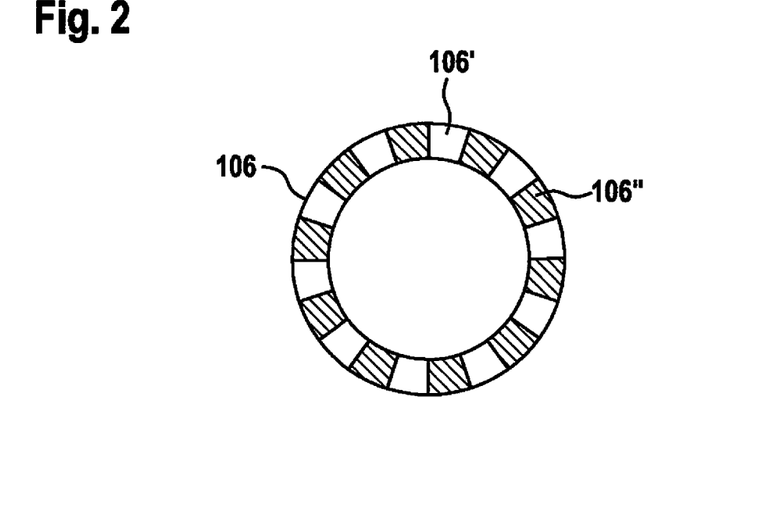
FIG. 2 shows an encoding device for use in the injection device according to a first specific embodiment of the present invention.

FIG. 2 is an encoding device for use in the injection device according to the first specific embodiment of the present invention.

As shown in FIG. 2, light-encoding device 106 is an annular coding disk, which has reflective regions 106' and non-reflective regions 106". Since the rotational angle is directly dependent on the dispensed dosage quantity, it is possible to use optical sensor device 100, 101, 102, 103, 104, 105 to directly ascertain the injected dosage quantity. The angular resolution depends on the special use and configuration and in particular is dependent on the resolution of reflective regions 106' and non-reflective regions 106".

Figure 3:
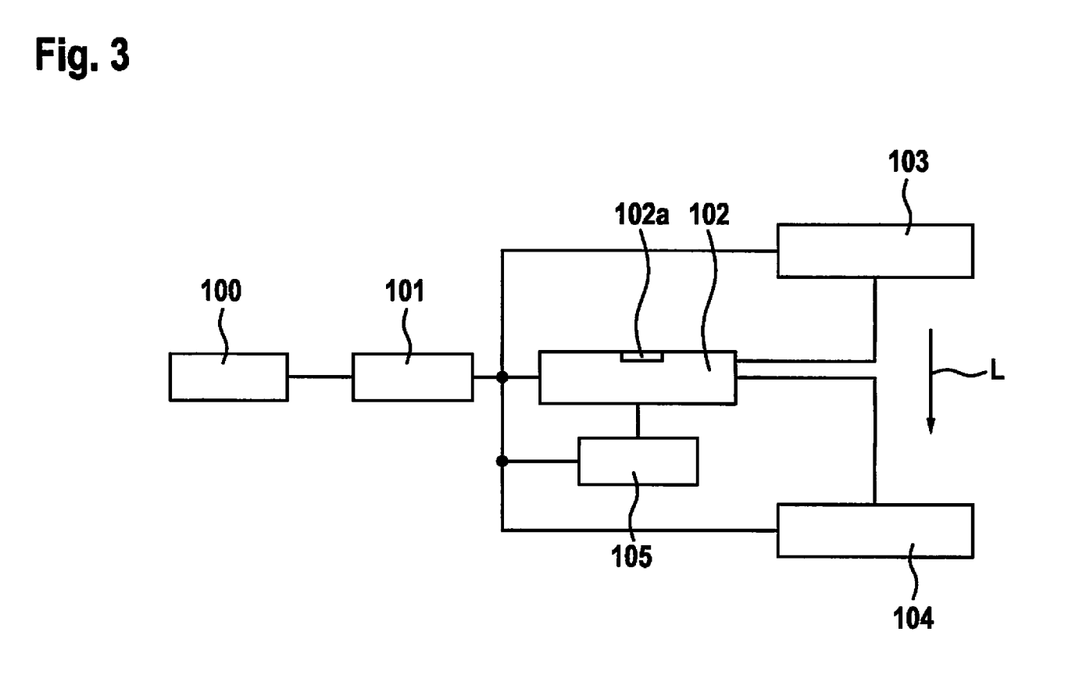
FIG. 3 shows a block diagram of the electrical circuit system in the injection device according to the first specific embodiment of the present invention.

FIG. 3 is a block diagram of the electrical circuit system in the injection device according to the first specific embodiment of the present invention and shows the electrical interconnection of components 100, 101, 102, 103, 104, 105.

Figure 4:
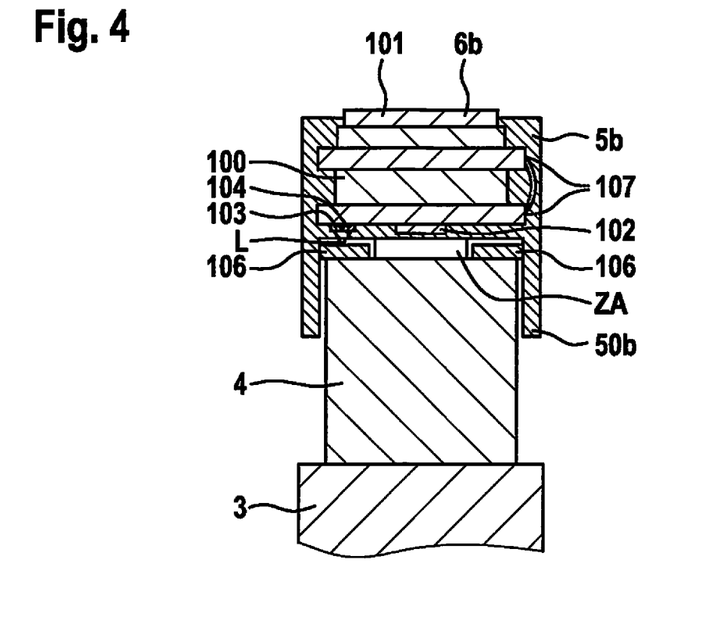
FIG. 4 shows a schematic, partial cross-sectional representation to describe an injection device according to a second specific embodiment of the present invention.

FIG. 4 is a schematic, partial cross-sectional representation to describe an injection device according to a second specific embodiment of the present invention.

In the second specific embodiment, the selector device is denoted by reference numeral 5b whereas the injection button bears reference numeral 6b.

The second specific embodiment differs from the first specific embodiment in that the mask-type light-encoding device 106 does not project beyond dosing sleeve 4 in the radial direction. As a result, it is possible to form an appendage 50b on selector device 5b, which laterally shields light-transmitting device 103 and light-receiving device 104 so that interference effects from external light sources are able to be minimized even further.

In all other respects, the configuration and the method of functioning of the second specific embodiment are similar to that of the afore-described first specific embodiment.

Figure 5:
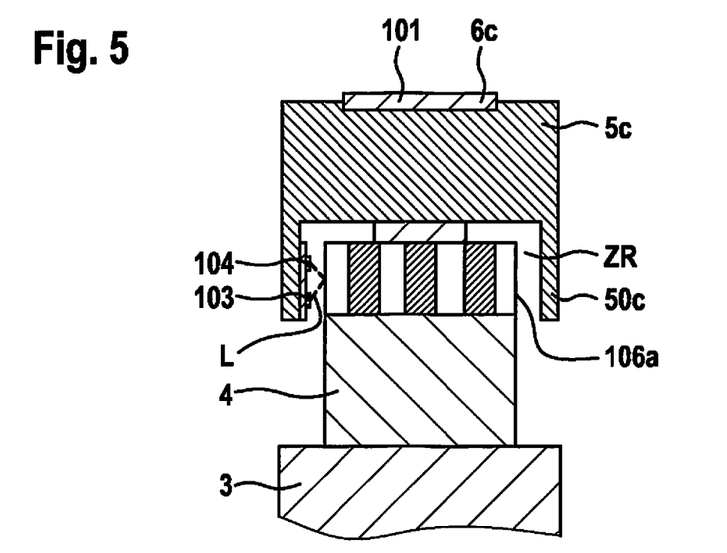
FIG. 5 shows a schematic, partial cross-sectional representation to describe an injection device according to a third specific embodiment of the present invention.

FIG. 5 is a schematic, partial cross-sectional representation to describe an injection device according to a third specific embodiment of the present invention.

In the third specific embodiment, the injection button is denoted by reference numeral 6c and the selector device bears reference numeral 5c. In this third specific embodiment, the selector device also has appendages 50c, which extend along dosing sleeve 4 in the axial direction. In this instance, light-encoding device 106a is provided on a radial outer periphery of dosing sleeve 4, and light-transmitting device 103 and light-receiving device 104 are provided in an oppositely situated region on appendage 50c of selector device 5c, separated by a radial interspace ZR between dosing sleeve 4 and selector device 5c.

Light-transmitting device 103 and light-receiving device 104 could then be realized on a flex foil on appendage 50c or the selector device could be configured as a molded interconnect device MID in order to integrate the electronics.

In all other respects, the configuration of the third specific embodiment is similar to that of the second specific embodiment. It is pointed out that for reasons of simplification, the placement of components 100, 107, 102 is not shown in selector device 5c but these components may also be present and integrated there in an appropriate manner as described earlier, or components 100 as well as 102 may likewise be situated on the flex PCB or the MID.

Figure 6:
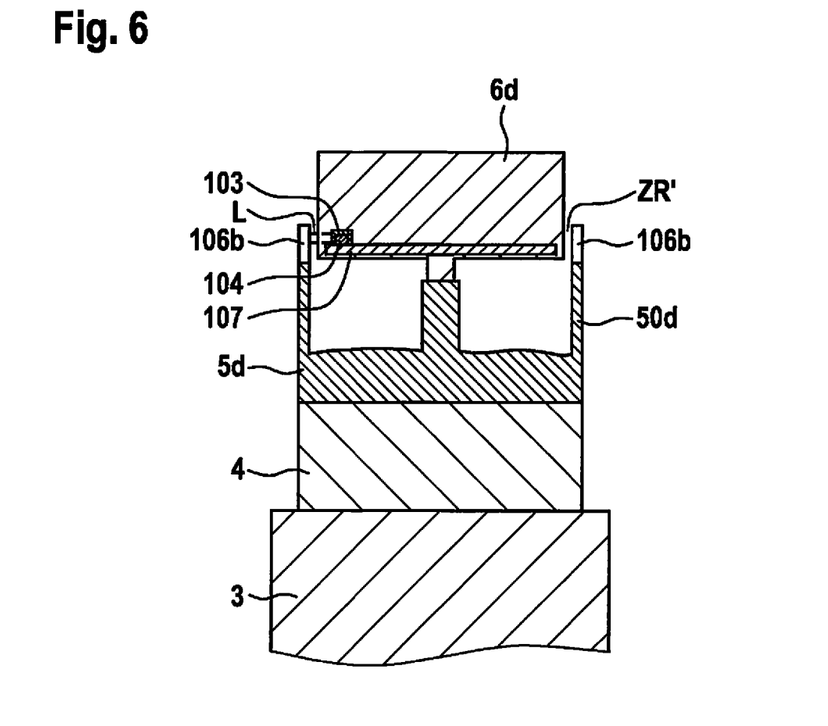
FIG. 6 shows a schematic, partial cross-sectional representation to describe an injection device according to a fourth specific embodiment of the present invention.

FIG. 6 is a schematic, partial cross-sectional representation to describe an injection device according to a fourth specific embodiment of the present invention.

In the fourth specific embodiment according to FIG. 6, the injection button bears reference numeral 6d whereas the selector device is provided with reference numeral 5d. In this specific embodiment, selector device 5d is permanently connected to dosing sleeve 4 whereas injection button 6d is supported so that it is able to rotate relative to selector device 5d. Light-encoding device 106b is provided on an axial appendage 50d of selector device 5d on the radial inner periphery of selector device 5d. Light-transmitting device 103 and light-receiving device 104 are provided in an oppositely situated region in injection button 6d, separated by a radial interspace ZR' between selector device 5d and injection button 6d. In this specific embodiment, dosing sleeve 4 executes the rotary motion relative to injection button 6d together with selector device 5d during the injection process.

In this specific embodiment, components 100, 101, 102, 103, 104, 105 are provided in injection button 6d. Here, too, these components are only partially shown in order to simplify matters, but the configuration generally corresponds to the configuration of the afore-described specific embodiments.

Figure 7:
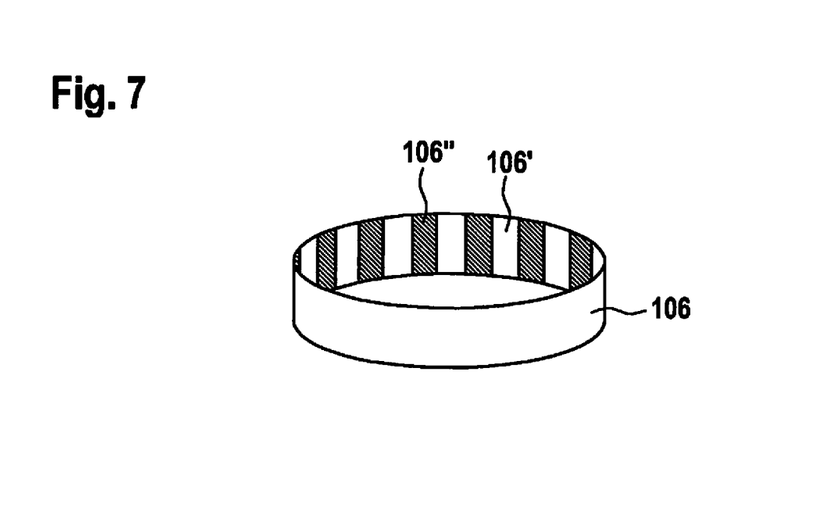
FIG. 7 shows an encoding device for use in the injection device according to the fourth specific embodiment of the present invention.

FIG. 7 is an encoding device for use in the injection device according to the fourth specific embodiment of the present invention.

In this example as well, light-encoding device 106b is an optical mask having reflective regions 106' and non-reflective regions 106" on the inner periphery of a sleeve, which is mounted on the radial inner periphery of selector device 5d in the region of appendage 50d.

Figure 8:
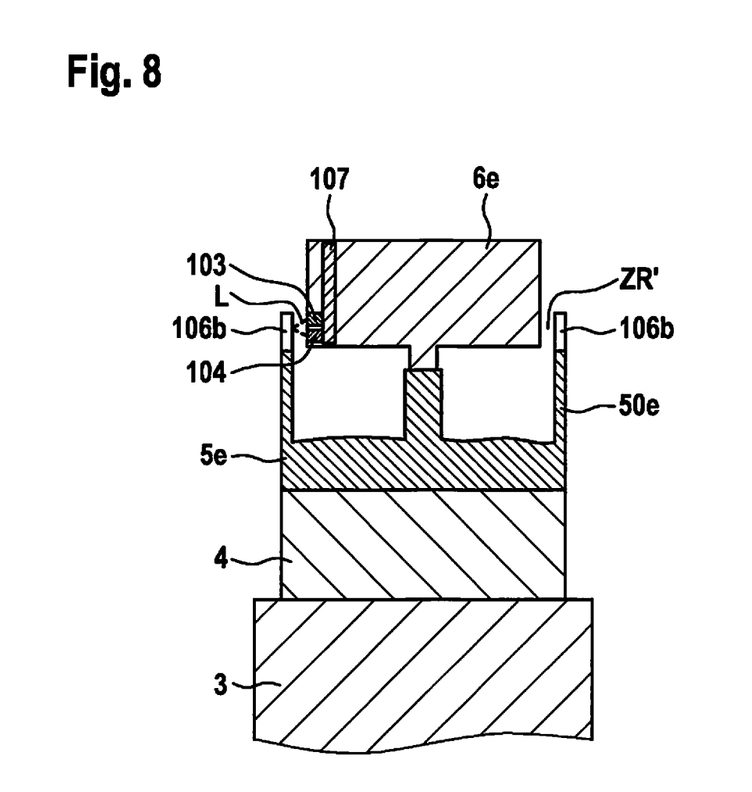
FIG. 8 shows a schematic, partial cross-sectional representation to describe an injection device according to a fifth specific embodiment of the present invention.

FIG. 8 is a schematic, partial cross-sectional representation to describe an injection device according to a fifth specific embodiment of the present invention.

In the fifth specific embodiment, the selector device is denoted by reference numeral 5e, the axial appendage is denoted by reference numeral 50e, while the injection button is denoted by reference numeral 6e.

The fifth specific embodiment essentially corresponds to the afore-described fourth specific embodiment, and only a different placement of circuit board device 107 in injection button 6e is schematically outlined.

In this specific embodiment, too, components 100, 101, 102, 103, 104, 105 are provided in injection button 6e. To simplify matters, these components are once again shown only partially but the configuration is generally similar to that of the afore-described specific embodiments.

Although the present invention has been described on the basis of exemplary embodiments, it is not restricted to these.

In particular, the mentioned materials and topologies are merely of an exemplary nature and not limited to the described examples.

Notwithstanding the fact that the present invention was described on the basis of exemplary embodiments, it is not restricted to these embodiments but is able to be modified in many different ways.

For example, it is conceivable to individually assign optical properties to each of the segments of the light-encoding device, e.g., through different graduations of the reflection. In this way, the optical sensor device is able to uniquely identify each angular section that rotates past the sensor device during the injection process and thus also identify a fill level memory, for instance. In addition, the present invention is not restricted to the afore-described geometries but may generally be used in all types of pen-type injection devices.

What is claimed is:

1. An injection device, comprising:
   a pen-type sleeve to accommodate a cartridge holder;
   a mechanical injection system, in the pen-type sleeve, which has a dosing sleeve by which a dosage quantity to be injected is predefinable and which is configured to execute a rotatory motion during an injection process;
   a selector device connected to the dosing sleeve for setting the dosage quantity to be injected;
   an injection button connected to the selector device for applying an injection force; and
   an optical sensor device to detect the rotatory motion of the dosing sleeve during injection of the dosage quantity, which has a signal-processing device for ascertaining and storing the injected dosage quantity based on the detected rotatory motion of the dosing sleeve;
   wherein the injection button has a switch device of the optical sensor device by which the optical sensor device is activatable during the application of the injection force,
   wherein the optical sensor device has a light-transmitting device, a light-receiving device, and a light-encoding device, which are positioned so that light emitted by the light-transmitting device impinges upon the light-encoding device before it impinges upon the light-receiving device, and
   wherein the light-encoding device has an annular development and includes reflective regions and non-reflective regions,
   wherein the light-encoding device is provided on or in a periphery of the dosing sleeve.

2. The injection device of claim 1, wherein the light-transmitting device, the light-receiving device, and the signal-processing device are integrated into the selector device.

3. The injection device of claim 2, wherein the injection button is removable from the selector device.

4. The injection device of claim 1, wherein the optical sensor device has an internal memory.

5. The injection device of claim 1, wherein the optical sensor device has a wireless or wired transmission device for transmitting the ascertained injected dosage quantity to an external memory device.

6. An injection device comprising:
   a pen-type sleeve to accommodate a cartridge holder;
   a mechanical injection system, in the pen-type sleeve, which has a dosing sleeve by which a dosage quantity to be injected is predefinable and which is configured to execute a rotatory motion during the injection process;
   a selector device connected to the dosing sleeve for setting the dosage quantity to be injected;

an injection button connected to the selector device for applying an injection force; and an optical sensor device to detect the rotatory motion of the dosing sleeve during the injection of the dosage quantity, which has a signal-processing device for ascertaining and storing the injected dosage quantity based on the detected rotatory motion of the dosing sleeve;

wherein the injection button has a switch device of the optical sensor device by which the optical sensor device is activatable during the application of the injection force, wherein the optical sensor device has a light-transmitting device, a light-receiving device, and a light-encoding device, which are positioned so that light emitted by light-transmitting device impinges upon the light-encoding device before it impinges upon the light-receiving device, and wherein the light-encoding device has an annular development and includes reflective regions and non-reflective regions, wherein the light-encoding device is provided on or in an axial outer periphery of the dosing sleeve, wherein the light-transmitting device and the light-receiving device are provided in an oppositely situated region on or in the selector device, separated by an axial interspace between the dosing sleeve and the selector device, and wherein the selector device is configured so that the dosing sleeve executes the rotary motion relative to the selector device during the injection process.

7. An injection device comprising:

a pen-type sleeve to accommodate a cartridge holder;

a mechanical injection system, in the pen-type sleeve, which has a dosing sleeve by which a dosage quantity to be injected is predefinable and which is configured to execute a rotatory motion during the injection process;

a selector device connected to the dosing sleeve for setting the dosage quantity to be injected;

an injection button connected to the selector device for applying an injection force; and an optical sensor device to detect the rotatory motion of the dosing sleeve during the injection of the dosage quantity, which has a signal-processing device for ascertaining and storing the injected dosage quantity based on the detected rotatory motion of the dosing sleeve;

wherein the injection button has a switch device of the optical sensor device by which the optical sensor device is activatable during the application of the injection force, wherein the optical sensor device has a light-transmitting device, a light-receiving device, and a light-encoding device, which are positioned so that light emitted by light-transmitting device impinges upon the light-encoding device before it impinges upon the light-receiving device, and wherein the light-encoding device has an annular development and includes reflective regions and non-reflective regions, wherein the light-encoding device is provided on or in a radial outer periphery of the dosing sleeve, wherein the light-transmitting device and the light-receiving device are provided in an oppositely situated region on or in the selector device, separated by a radial interspace between the dosing sleeve and the selector device, and wherein the selector device is configured so that the dosing sleeve executes the rotatory motion relative to the selector device during the injection process.

8. An injection device comprising:

a pen-type sleeve to accommodate a cartridge holder;

a mechanical injection system, in the pen-type sleeve, which has a dosing sleeve by which a dosage quantity to be injected is predefinable and which is configured to execute a rotatory motion during the injection process;

a selector device connected to the dosing sleeve for setting the dosage quantity to be injected;

an injection button connected to the selector device for applying an injection force; and an optical sensor device to detect the rotatory motion of the dosing sleeve during the injection of the dosage quantity, which has a signal-processing device for ascertaining and storing the injected dosage quantity based on the detected rotatory motion of the dosing sleeve;

wherein the injection button has a switch device of the optical sensor device by which the optical sensor device is activatable during the application of the injection force, wherein the optical sensor device has a light-transmitting device, a light-receiving device, and a light-encoding device, which are positioned so that light emitted by light-transmitting device impinges upon the light-encoding device before it impinges upon the light-receiving device, and wherein the light-encoding device has an annular development and includes reflective regions and non-reflective regions, wherein the light-encoding device is provided on or in a radial inner periphery of the selector device, wherein the light-transmitting device and the light-receiving device are provided in an oppositely situated region on or in the injection button, separated by a radial interspace between the selector device and the injection button, and wherein the injection button is configured so that the dosing sleeve executes the rotatory motion relative to the injection button together with the selector device during the injection process.

9. The injection device of claim 8, wherein the light-transmitting device, the light-receiving device, and the signal-processing device are integrated into the injection button.

10. A method for providing injection-measuring, the method comprising:

providing an injection device having a pen-type tube for accommodating a cartridge holder; a mechanical injection system provided in the pen-type tube, which has a dosing sleeve by which a dosage quantity to be injected is predefinable and which is configured to execute a rotatory motion during the injection process; a selector device, connected to the dosing sleeve, for adjusting the dosage quantity to be injected; and an injection button, connected to the selector device, for applying an injection force;

detecting the rotatory motion of the dosing sleeve during the injection of the dosage quantity with an optical sensor device; and ascertaining and storing the injected dosage quantity based on the detected rotatory motion of the dosing sleeve with a signal-processing device of the optical sensor device, wherein the injection button has a switch device of the optical sensor device by which the optical sensor device is activated when applying the injection force, wherein the optical sensor device has a light-transmitting device, a light-receiving device, and a light-encoding device, which are positioned so that light emitted by the light-transmitting device impinges upon the light-encoding device before it impinges upon the light-receiving device, and wherein the light-encoding device has an annular development and includes reflective regions and non-reflective regions, wherein the light-encoding device is provided on or in a periphery of the dosing sleeve.

11. The method of claim 10, wherein the optical sensor device has an internal memory and the dosage quantity is stored in the internal memory.

12. The method of claim 10, wherein the optical sensor device has a wireless or wired transmission device for transmitting the ascertained injected dosage quantity to an external memory device and the dosage quantity is transmitted to the external memory device.

* * * * *